United States Patent [19]

Dang Vu et al.

[11] Patent Number: 4,943,669
[45] Date of Patent: Jul. 24, 1990

[54] METHOD ACCORDING TO THE INVENTION IS NOTABLY APPLIED TO THE SELECTIVE DIMERIZATION OF PROPYLENE INTO METHYL-4-PENTENE-1

[75] Inventors: Quang Dang Vu, Neuilly; Yves Chauvin, Le Pecq, both of France

[73] Assignee: Institut Francais Du Petrole, Rueil-Malmaison, France

[21] Appl. No.: 370,530

[22] Filed: Jun. 23, 1989

[30] Foreign Application Priority Data

Jun. 24, 1988 [FR] France ............................ 88 08633

[51] Int. Cl.$^5$ .......................... C07C 2/00; C07C 2/08
[52] U.S. Cl. .................................... 585/503; 585/510; 585/910; 585/911; 585/921; 585/922; 585/924; 585/925; 585/926; 422/200
[58] Field of Search ............... 585/503, 510, 910, 911, 585/921, 922, 923, 924, 925, 926

[56] References Cited

U.S. PATENT DOCUMENTS 4,544,544 10/1985 Dang Vu et al. .................. 423/360
4,709,111 11/1987 Ward ................................. 585/503

Primary Examiner—Chung K. Pak
Attorney, Agent, or Firm—Millen, White & Zelano

[57] ABSTRACT

The invention provides a catalytic method for the dimerization or codimerization or oligomerization, particularly selectively, of olefins, carried out under pressure, in a reaction zone 1 containing a solid catalyst bed into which is disposed a plurality of hollow internal spaces 6.3 defined by walls and through which an autogenous thermoregulation fluid flows, in the form of a sheet, after passing through a central distributing zone 6.1 and distributing zones 6.2 and before passing through collecting zones 6.4 and into a central collecting zone 6.5.

6 Claims, 2 Drawing Sheets

METHOD ACCORDING TO THE INVENTION IS NOTABLY APPLIED TO THE SELECTIVE DIMERIZATION OF PROPYLENE INTO METHYL-4-PENTENE-1

BACKGROUND OF THE INVENTION

1. Field of the Invention

The invention relates to a method for carrying out, generally under pressure, the (notably selective) dimerization, codimerization and oligomerization of olefins in the presence of at least one catalyst, usually solid, in at least one reaction zone whose temperature is controlled by a heat-exchange device with hollow plates disposed therein.

Generally, in this type of reactions, when operating in accordance with the invention, at least one of the reagents is either in the liquid state, or in a state making circulation thereof by means of a pump possible (supercritical state), such that the ratio Tr between the temperature T (in Kelvin degrees) of the reagent system and the (pseudo) critical temperature Tc (in Kelvin degrees) of said system is preferably less than 2, for example than 1.5.

The olefin used may more particularly be chosen from ethylene, propylene, styrene, one of the isomers of the butenes or one of the mixtures thereof. This olefin may be used in the pure state or mixed with one or more compounds not reacting on the catalyst in the conditions used, such for example as cyclic or acyclic saturated hydrocarbons, in particular those having from 2 to 10 carbon atoms. The olefin concentration in the mixture may be from 5 to 100%, preferably from 10 to 100% by weight.

The invention relates more particularly to a method for the selective dimerization of propylene into methyl-4 pentene-1, for example by means of solid potassium and/or sodium based catalysts.

2. Description of the Prior Art

It is known to dimerize or oligomerize olefins in the homogeneous liquid phase so as to obtain, for example, C6 dimates (U.S. Pat. Nos. 4,283,305 and 4,366,087 belonging to the Applicant.

It is much more difficult to carry out selective dimerization when using a heterogeneous catalyst, for example for dimerizing propylene into methyl-4 pentene-1, with sufficient selectivity, particularly greater than 85%. It is in fact then necessary to maintain a relatively constant temperature, within fairly narrow limits, below which the activity of the catalysts drops to a value which makes the reaction industrially unusable and above which consecutive isomerization reactions take place, lower the activity and cause practically insurmountable separation problems.

The isotherm reaction system the most often used is the single pass calender tube reactor where the inside of the tubes is filled with catalyst and thus forms the reaction medium. But, in selective dimerization, the catalytic system generally undergoes spontaneous and/or accidental (due to impurities) de-activation, which requires the periodic renewal of this catalyst, a technical constraint which is difficult to put into practice with a reactor in which the high number of tubes must be filled and emptied one by one manually. It is also known, when the temperature of the reaction is to be maintained within relatively narrow limits, to place in the catalyst bed a heat transfer apparatus either tube-based (GB No. 2,046,618), or plate-based (U.S. Pat. No. 3,666,423) or grid-based (U.S. Pat. No. 4,693,807), and to cause a fluid to flow inside this apparatus for providing heat transfer and commonly designated under the name of thermoregulation fluid.

The drawback in the use of a tube-based heat transfer apparatus is due to the fact that the connection between these individual tubes is very cumbersome and, consequently, it is very difficult to correctly fit the assembly inside the reactor. The drawback of the plate based heat transfer apparatus of U.S. Pat. No. 3,666,423 is its bulk and its low efficiency. In order to withstand the reaction pressure, the plates are only partially hollow and the thermoregulation fluid thus has only a small portion of the area of the plates for carrying out its exchange work.

In his U.S. Pat. No. 4,544,544, the Applicant has proposed, for gas reagent systems, a method for using hollow plates, made from thin metal sheets and with rectangular internal section.

The plates used in the methods of the present invention work very little under stress, which makes it possible to hollow them out completely and to let the thermoregulation fluid provide the exchange through the whole of the available area. In addition, fitting and connections are sufficiently simple so as to be readily carried out in the restricted space offered by the reactor.

SUMMARY OF THE INVENTION

The present invention uses a continuous single-stage reaction system equipped with a heat transfer plate apparatus. FIG. 3 explains the operation of the unit:
  the reaction fluid will first of all be used as thermoregulation fluid for the unit and the catalyst bed; then it will flow through the solid catalyst bed enclosed in an envelope 1 substantially cylindrical and elongate in shape;
  the inside of the catalyst bed is cooled by the flow of thermoregulation fluid which flows through a heat exchange device disposed in said catalyst bed and comprising hollow plates manufactured, for example, from thin flat or corrugated metal sheets as will be explained further on;
  the thermoregulation fluid flowing inside the plates comprises the reagent(s) forming the fresh charge, the flow of this fluid being usually provided by at least one pump 13;
  the thermoregulation system is a system open on the reaction system; in fact, it is continuously fed by the make-up reagent(s) which pass directly from the thermoregulation system into the reactor without any permanent or transitory mechanical barrier.

According to the method of the invention, the fresh charge (e.g. liquid propylene) is fed, under a pressure generally between 1.2 and 12 MPa, into the duct 8 of the manufacturing unit (manufacturing for example methyl-4 pentene-1).

This fresh charge is first of all preferably preheated indirectly by the hot reaction effluent (coming from duct 5) through the heat exchanger 9. It then passes into duct 10 and meets a recycled fraction of the thermoregulation fluid which will be called "recycled charge" hereafter, this recycled fraction being conveyed by duct 11.

The weight ratio between the recycled charge and the fresh charge is usefully between 1 and 500, preferably between 2 and 200 and even more preferably between 5 and 100.

The mixture thus obtained (fresh charge plus recycled charge) forms the thermoregulation fluid (or heat-carrying fluid) of the reactor 1. This fluid, which is generally between 100° and 200° C., preferably about 150° C., and at a reduced temperature of about 1.13, and in a state such that it may still be conveyed by a pump, penetrates into duct 2 inside the hollow coolant plates 6.3 disposed within the catalyst bed contained in the reactor 1.

The thermoregulation fluid absorbs the reaction heat released as the product of synthesis is formed (e.g. methyl-4 pentene-1 obtained by selective dimerization of propylene). This heat-carrying fluid leaves reactor 1 through duct 3.

It is then separated into two portions. A first portion forms the charge to be processed which will flow through the catalyst bed. This charge will hereafter be called "make-up charge". It is fed to reactor 1 through duct 14. A second portion of the thermoregulation fluid drawn off through duct 3 will be recycled through duct 11 into the heat exchange plates 6.3 (mixed with some fresh charge from duct 10). This second portion of thermoregulation fluid is called "recycled charge".

The "recycled charge" passes through duct 12 where it is drawn in by pump 13 (preferably centrifugal) to be injected into duct 11 already mentioned.

In accordance with the characteristics of the invention, the weight ratio between the recycled charge and the make-up charge is advantageously between 1 and 500, preferably between 2 and 200 and even more preferably between 5 and 100. Too low a ratio prevents satisfactory heat control within the catalyst bed; too high a ratio requires a flow section such that the hollow plates become too thick and very cumbersome. The "make-up charge", not taken up by the pump 13, passes into duct 14 through the exchanger 15 whose purpose is to re-adjust the temperature at the input to reactor 1 to the desired level. This make-up charge leaves exchanger 15 through duct 4 and then passes through the catalyst bed contained in reactor 1. The resultant reaction effluent is discharged from the reactor through duct 5 for preheating the fresh charge through exchanger 9. From 9, said effluent is usefully directed, through duct 16, to a distillation and conditioning unit (not shown in the figure).

When it is a question of dimerizing propylene selectively into methyl-4 pentene-1, an alkaline carbonate based catalyst for example is used preferably impregnated by the metal of the same family.

Because of the good heat control provided by the plate cooling system, it has been possible to push the conversion very far without the selectivity of the operation being affected thereby.

Thus, the invention has as object a catalytic method for dimerizing or codimerizing or oligomerizing olefins carried out usually under pressure, in the presence of a solid catalyst, in a reaction zone defined by a substantially cylindrical enclosure whose section is substantially circular, said enclosure containing a generally fixed catalyst bed in which a plurality of hollow internal spaces is disposed, through which flows a thermoregulation fluid, at a pressure substantially equal to the pressure to which the reaction mixture is subjected, in which method:

a fresh liquid charge, containing at least one olefin, mixed with a recycled charge defined below, is introduced into said hollow internal spaces defined by walls, the weight ratio between the recycled charge and the fresh charge being between 1 and 500, the fresh charge-recycled charge mixture forming the thermoregulation fluid;

the thermoregulation fluid is drawn off from said hollow internal spaces and this fluid is separated into two portions called hereafter recycled charge and make-up charge, the weight ratio between said recycled charge and said make-up charge being between 1 and 500;

said recycled charge is fed into said hollow internal spaces as thermoregulation fluid component;

said make-up charge is fed into said catalyst bed;

a reaction effluent is drawn off from said catalyst bed.

The invention also relates to the implementation of said method with the use of hollow internal spaces of special design for the flow of the thermoregulation fluid.

DESCRIPTION OF THE PREFERRED EMBODIMENTS

Figure 1:
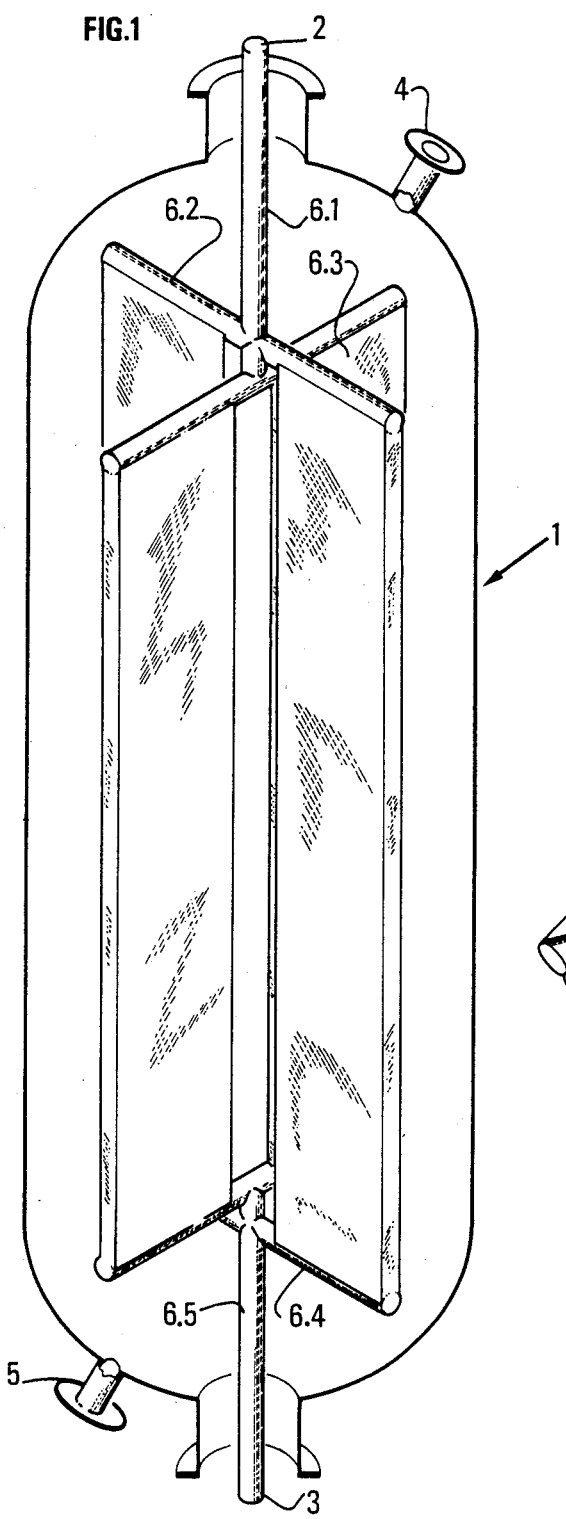
FIG. 1 shows a reactor having hollow internal spaces (plates).

In FIG. 1, the hollow internal spaces (or plates) have flat faces. FIGS. 2A, 2B, 2C and 2D show improved plates in accordance with the invention.

In FIG. 1 is shown an enclosure 1, of substantially cylindrical shape and whose cross section has a substantially circular form, comprising at least one duct 2 for introducing a thermoregulation fluid, at least one duct 3 for drawing off said fluid, at least one duct 4 for introducing a so-called make-up charge into the enclosure and at least one duct 5 for drawing off the reaction effluent from said enclosure. The enclosure 1 further comprises:

(a) at least one central distributing collector 6.1, for example vertical, whose axis corresponds generally to the axis of the enclosure, which is situated in the upper part of the enclosure and is connected to duct 2, (b) a plurality of distributing collectors 6.2, perpendicular to the axis of the enclosure, these collectors being connected individually to the central distributing collector 6.1, (c) at least one central receiving collector 6.5, for example vertical, whose axis corresponds generally to the axis of the enclosure, which is situated in the lower part of the enclosure and is connected to duct 3, (d) a plurality of receiving collectors 6.4, perpendicular to the axis of the enclosure, these collectors being connected individually to the central receiving collector 6.5, (e) plurality of hollow continuous and elongate plates intended for the flow of the thermoregulation fluid, each plate comprising an opening on a distributing collector 6.2 and an opening on a receiving collector 6.4.

The faces of said hollow plates may be formed by corrugated metal sheets whose corrugations may be chosen from one of the following forms: square, rectangular, triangular, sinusoidal and a herring bone pattern (see FIG. 2D), the aim being to create a high turbulence in the flow of the thermoregulation fluid.

It is desirable for said hollow plates to be substantially parallelepipedic 6.3, each plate comprising two wide parallel faces defining a plane disposed radially with respect to the axis of the enclosure and four thin faces, two of them being parallel to the axis, each plate being connected, by its upper thin face perpendicular to the axis of the enclosure, to a distributing collector 6.2 and, by its lower thin face perpendicular to the axis of the enclosure, to a receiving collector 6.4. These four thin faces may possibly be not flat, but for example semi-cylindrical.

In this case it should be noted that, in each of said substantially parallelepipedic hollow plates, adjacent channels can be formed by means of corrugated sheets so as to improve the flow of the thermoregulation fluid, the sections of said channels being chosen from one of the following forms: square, rectangular, (see FIG. 2A), triangular (see FIG. 2B), sinusoidal (see FIG. 2C), the channels connecting together the two thin faces perpendicular to the axis of the enclosure of the same plate.

In a variant of the invention, the hollow plates may possibly have different widths, which allows a minimum ratio to be maintained between the volume of the enclosure and the exchange area, while avoiding too great a distance between any point of the enclosure and the nearest plate.

The metal sheets which may be used in the different embodiments of the invention generally have less than 10 mm thickness, preferably less than 3 mm thickness.

In FIG. 1, given by way of example, the path of the thermoregulation fluid through substantially parallelepipedic hollow plates (or hollow internal spaces) will be described. The charge, in the form of make-up charge, penetrates into enclosure 1 through duct 4, passes through the catalyst bed contained in said enclosure, then leaves said enclosure, in the form of a reaction effluent, through duct 5. The autogenous (i.e. formed by one or more components constituting the fresh charge) thermoregulation fluid passes from duct 2 into the central distributing collector 6.1. It is then divided between the distributing collectors 6.2. Then it penetrates into each of the hollow plates 6.3 through their upper thin face perpendicular to the axis of the enclosure, these hollow plates being disposed within the catalyst bed contained in enclosure 1. The fluid flows down inside said hollow plates in the form of a sheet. On leaving the hollow plates, it is collected in the receiving collectors 6.4 individually connected to the central receiving collector 6.5 into which the fluid then passes. Finally, the thermoregulation fluid leaves through duct 3.

The advantage of an autogenous thermoregulation fluid is, on the one hand, that there is no pressure difference between the inside and the outside of the plates (apart from that created by the pressure losses due to the flow of the different fluids) and, on the other hand, that in the case of a leak there is no danger of pollution of the catalytic system.

In brief, in the improved invention:
   the autogenous thermoregulation fluid (formed by the component(s) constituting the fresh charge (and so the recycled charge)) is fed through a central distributing zone 6.1,
   said fluid from the central distributing zone 6.1 is divided up into distributing zones 6.2,
   said fluid is fed, from said distributing zones 6.2, into said hollow internal spaces 6.3, defined by walls (said spaces having a substantially parallelepipedic shape, each space 6.3 then comprising two wide parallel faces defining a plane disposed radially with respect to the axis of the reaction zone 1 and four thin faces, two of which are parallel to the axis of the reaction zone and the other two being perpendicular to this axis), through their thin upper face perpendicular to the axis of the reaction zone 1,
   said fluid is caused to flow inside said hollow internal spaces 6.3 in the form of a sheet,
   said thermoregulation fluid is discharged from said hollow internal spaces 6.3 through their thin lower face perpendicular to the axis of the reaction zone 1, into collecting zones 6.4 which are connected to a central collecting zone 6.5 from which said fluid is then drawn off.

Figure 3:
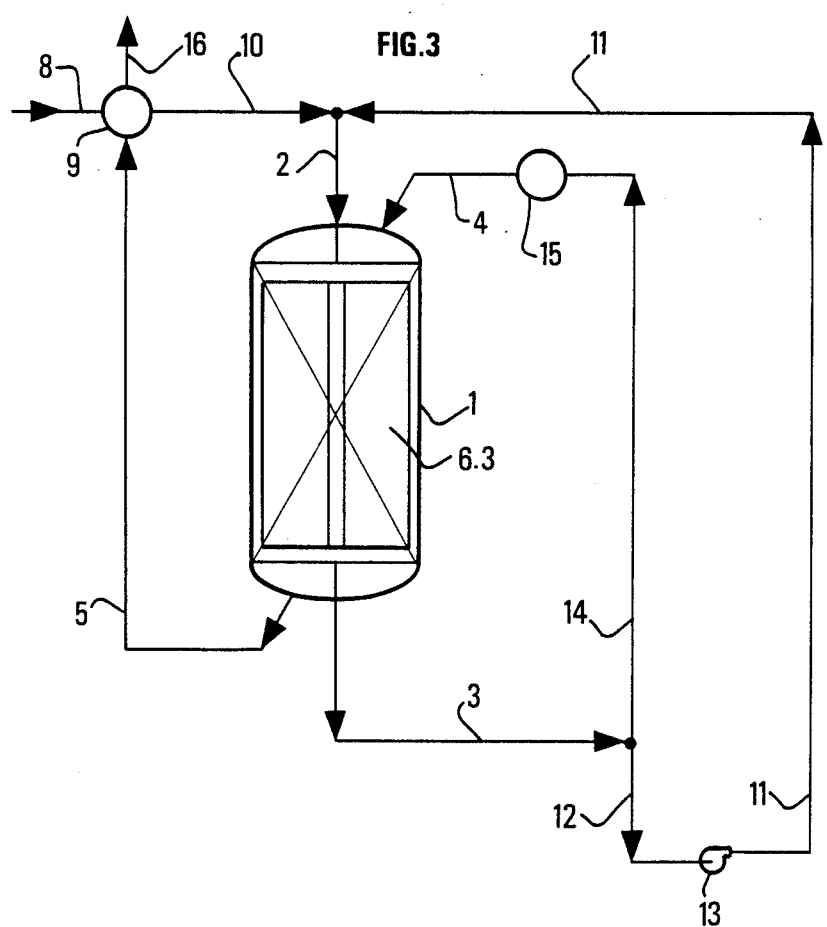
FIG. 3 explains the operation unit.

In FIGS. 1 and 3 enclosure 1 is shown in a substantially vertical position; the flow of the thermoregulation fluid and of the make-up charge may take place from top to bottom as described above, but also from bottom to top (and so also contraflow wise).

In addition, in FIGS. 1 and 3, the duct 4 for intake of the (make-up) charge has been shown arbitrarily at the top of enclosure 1 and duct 5 for drawing off the reaction effluent at the base of enclosure 1, but these ducts 4 and 5 may in fact be situated at any adequate level of the enclosure.

FIG. 1 shows an axial reactor (enclosure) in which the reagents pass through the catalyst bed parallel to the axis of the reactor.

The invention may also be applied to a radial reactor comprising a permeable basket in the form of a cylindrical ring, defined for example by two coaxial cylinders, in which the catalyst and the hollow plates are disposed and where the reagents pass through the bed perpendicularly to the axis of the reactor.

Figure 2A:
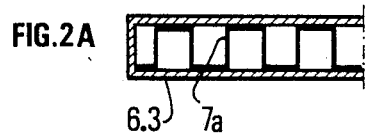
FIGS. 2A, 2B, 2C and 2D show plates in accordance with invention.
Figure 2B:
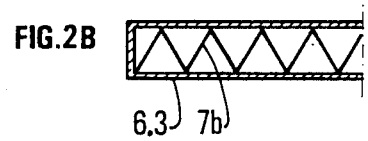
Figure 2C:
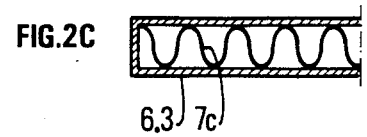
Figure 2D:
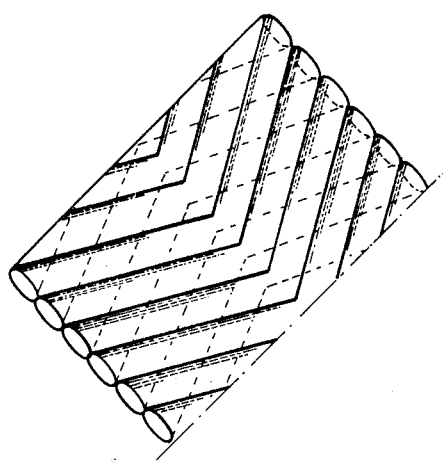

FIGS. 2A, 2B and 2C show three substantially parallelepipedic hollow plates 6.3 in which adjacent channels 7A, 7B and 7C are formed by means of corrugated metal sheets, the sections of said channels being chosen from one of the following forms: square, rectangular (7A), triangular (7B) and sinusoidal (7C), these channels connecting together the two thin faces perpendicular to the axis of the enclosure of the same plate: on the one hand, the presence of these adjacent channels ensures the strength of the hollow plates 6.3 which may reach and exceed for example 10 meters in height and, on the other hand, it avoids the formation of dead zones which might be formed because of the sheet flow of the thermoregulation fluid inside the plates.

The metal sheets may be assembled together either by welding, or much more economically by brazing, either by points or by immersion into a bath, or any other adequate technique.

The invention is illustrated by the following examples:

EXAMPLE 1 (according to the invention)

In a vertical cylindrical reactor, 0.5 m in diameter, equipped with a hollow plate thermoregulation system in accordance with FIGS. 1 and 2A, a catalyst is disposed obtained by depositing 3.5% by weight of sodium or potassium carbonate flakes bonded by 1.5% of graphite and previously activated at 230° C. for 3 hours. Then, the unit shown in FIG. 3 is filled under a pressure of 9 MPa (through duct 8) with propane and a flowrate of 300 m³/h is provided by means of a pump 13.

By means of the external steam heater 15, the temperature of the propane is progressively raised. When this temperature reaches about 150° C., polypropylene is introduced in to the unit (through duct 8), while draining the propane through duct 16.

After a few hours, stationary state is established with a propylene flowrate of 5 m$^3$/h, 28.3% conversion of propylene into methyl-4 pentene-1 and a selectivity of 89.1%. This state was able to be maintained for several hundred hours without substantial variation of the conversion of propylene and the methyl-4 pentene-1 selectivity.

EXAMPLE 2 (comparative)

The same catalyst is used as in example 1, which is disposed in the same reactor from which the thermoregulation system of the invention has been removed, the hourly flowrate of propylene being identical.

The temperature of the propylene supplied to the reactor is 130° C. The temperature of the reaction effluent leaving the reactor is 190°C.

It will be noted that the conversion of the propylene does not exceed 15.0% and the methyl-4 pentene-1 selectivity only reaches 65.1%, the major part of the by-products of the reaction being formed by methyl-4 pentene-2.

It will be observed in addition that after 50 hours or so the catalyst lost a great part of its activity.

What is claimed is:

1. A catalytic method for dimerizing or codimerizing or oligomerizing olefins, carried out under pressure, in the presence of a solid catalyst, in a reaction zone defined by a substantially cylindrical enclosure whose section is substantially circular, said enclosure containing a catalyst bed in which a plurality of hollow internal spaces having a substantially parallelepipedic shape is disposed, through which flows a thermoregulation fluid, at a pressure substantially equal to the pressure to which the reaction mixture is subjected, in which method:

a fresh liquid charge, containing at least one olefin, mixed with a recycled charge defined below, is introduced into said hollow internal spaces defined by walls, the weight ratio between the recycled charge and the fresh charge being between 1 and 500, the fresh charge-recycled charge mixture forming the thermoregulation fluid;

the thermoregulation fluid is drawn off from said internal spaces and this fluid is separated into two portions called hereafter recycled charge and make-up charge, the weight ratio between said recycled charge and said make-up charge being between 1 and 500;

said recycled charge is fed into said internal spaces as a thermoregulation fluid component;

said make-up charge is fed into said catalyst bed; and a reaction effluent is drawn off from said catalyst bed.

2. A method according to claim 1 wherein said fresh charge is preheated by indirect contact with the reaction effluent.

3. A method according to claim 1 wherein the weight ratio between said recycled charge and said fresh charge is between 2 and 200.

4. A method according to claim 1 wherein the weight ratio between said recycled charge and said make-up charge is between 2 and 200.

5. A method according to claim 1 wherein:

the thermoregulation fluid is fed into a central distributing zone, the fluid from the central distributing zone is divided among distributing zones, said fluid is fed, from said distributing zones, into said hollow internal spaces defined by walls, each hollow internal space having substantially a parallelepipedic shape, through their thin upper face perpendicular to the axis of said reaction zone, said fluid is caused to flow inside said hollow internal spaces in the form of a sheet, said thermoregulation fluid is discharged from said hollow internal spaces, through their lower thin face perpendicular to the axis of the reaction zone, into collecting zones which are connected to a central collecting zone through which said fluid is then drawn off.

6. A method according to claim 1 wherein propylene is selectively dimerized to methyl-4-pentene.

* * * * *

UNITED STATES PATENT AND TRADEMARK OFFICE
CERTIFICATE OF CORRECTION

PATENT NO. : 4,943,669
DATED : July 24, 1990
INVENTOR(S) : Quang DANG et al,

It is certified that error appears in the above-identified patent and that said Letters Patent is hereby corrected as shown below:

Col. 8, Claim 6, Line 43:

Reads: - - -

( is selectively dimerized to methly-4-pentene. )

Should read: - - -

" is selectively dimerized to methyl-4-pentene-1. "

Signed and Sealed this

Twenty-fifth Day of May, 1993

Attest:

MICHAEL K. KIRK

Attesting Officer

Acting Commissioner of Patents and Trademarks